United States Patent
Biryukov et al.

(10) Patent No.: US 6,518,058 B1
(45) Date of Patent: Feb. 11, 2003

(54) METHOD OF PREPARING POLYPEPTIDES IN CELL-FREE SYSTEM AND DEVICE FOR ITS REALIZATION

(75) Inventors: Sergey Vladimirovich Biryukov, Moscow (RU); Peter Nikolayevich Simonenko, Moscow (RU); Vladimir Anatolievich Shirokov, Moscow (RU); Sergey Gennadievich Mayorov, Moscow (RU); Alexander Sergeyevich Spirin, Moscow (RU)

(73) Assignee: Roche Diagnostics GmbH (DE)

(*) Notice: Subject to any disclaimer, the term of this patent is extended or adjusted under 35 U.S.C. 154(b) by 0 days.

(21) Appl. No.: 09/647,316

(22) PCT Filed: Mar. 27, 1999

(86) PCT No.: PCT/EP99/02124

§ 371 (c)(1),
(2), (4) Date: Apr. 23, 2001

(87) PCT Pub. No.: WO99/50436

PCT Pub. Date: Oct. 7, 1999

(30) Foreign Application Priority Data

Mar. 31, 1998 (RU) .......... 98105294

(51) Int. Cl.⁷ .......... C12M 1/12
(52) U.S. Cl. .......... 435/297.2; 435/68.1; 435/69.1; 435/297.4
(58) Field of Search .......... 435/297.2, 297.4, 435/297.5, 68.1, 69.1, 175, 182

(56) References Cited

U.S. PATENT DOCUMENTS

| | | | |
|---|---|---|---|
| 4,786,597 A | 11/1988 | Matson et al. | 435/41 |
| 5,135,853 A | 8/1992 | Dziewulski et al. | 435/41 |
| 5,605,838 A * | 2/1997 | Hu et al. | 435/297.2 |

FOREIGN PATENT DOCUMENTS

| | | | |
|---|---|---|---|
| EP | 0593757 A1 | 4/1994 | C12P/21/00 |
| WO | WO 94/18341 | 8/1994 | C12P/21/02 |

* cited by examiner

Primary Examiner—David A. Redding
(74) Attorney, Agent, or Firm—Kenneth J. White; Roche Diagnostic Corporation

(57) ABSTRACT

The present invention provides a method for synthesis polypeptides in a cell-free system by which products of synthesis are branched in a low molecular weight fraction and a fraction which contains high molecular weight components with the target polypeptide, the main part of the low molecular weight fraction is removed via at least one part of the second porous barrier, the ratio of the volume of the fractions of feed solution and expendable components to the volume of the fraction containing the target polypeptide is chosen, modes of supply of the feed solution and expendable components of the fraction are realized.

7 Claims, 11 Drawing Sheets

Content of the
fixed volume
(batch)

Control

Content of the
reaction cell

METHOD OF PREPARING POLYPEPTIDES IN CELL-FREE SYSTEM AND DEVICE FOR ITS REALIZATION

FIELD OF INVENTION

The present invention concerns to molecular biology and biotechnology, namely to the methods and devices for synthesis of polypeptides in cell-free translation system.

BACKGROUND OF THE INVENTION

Several methods of polypeptide synthesis in cell-free translation system are known. For elimination of restrictions connected with a lower output of target polypeptides and short-term operation of cell-free translation systems a method was suggested which is widely used now (Spirin et al., 1988). This method is based on the principle of continuous removal from a reaction mixture of reaction products and continuous restoration of the initial concentration of low molecular weight components during synthesis. This method underlies several inventions connected with its improvement for increasing the synthesized product output (Alkahov et al., 1991; Baranov et al., 1993; Alakhov et al., 1995).

By the input of feeding solutions and removal of products of synthesis the known methods can be divided as follows: (a) methods in which dialysis is used to add feed solution components to the reaction mixture and to remove low molecular weight components from the reaction mixture through the dialysis membrane or to simultaneously remove low and high molecular weight components from the reaction mixture; (b) methods in which continuous ultrafiltration is used for a simultaneous removing of low and high molecular weight components of products through the membrane and a simultaneous input of feeding solutions directly into the reaction mixture volume or through the membrane; c) methods in which periodic input of a feed solution into the reaction mixture and subsequent removing of low and high molecular weight components through the membrane are used. Input and output of the flows is realized by changing the direction of liquid flows at the exposure of consecutive creation of pulses of positive or negative pressure.

The method (Mozayeny, 1995) is known in which the removal of products with large molecular weight is improved by increasing the area of a ultrafiltration membrane in relation to the reaction mixture volume. One of the main disadvantages of the given invention is that during removal of high molecular weight components through the large area of the membrane with the pore size of 70 kD to 100 kD, together with the final product useful working components of molecular weight up to 100 kD are lost. This is a limiting factor for the operating time of the cell-free system. The larger is the membrane area, the greater is the amount of high molecular components of the cell-free system washed-off from the reactor at a high flow rate. Another disadvantage is the necessity to use an external loop for creation of a tangential flow of the reaction mixture along the membrane surface. During passage of the reaction mixture via liquid communications three factors influence the work of the cell-free systems: (1) when the reaction mixture passes via the loop the feed solution is not added in the part of external volume of the reaction mixture, (2) low weight products which inhibit the cell-free system are not removed from the external volume, (3) the liquid communications and pumps are not thermostable and the reaction mixture changes its temperature depending on the environment. This leads to irreproducibility of results and limits the life time of the cell-free system.

The method in which authors offer to apply repeated pulse for input of the feeding solution in the reactor and removal of low and high molecular weight products of synthesis from the reactor via a membrane is known (Fischer et al., 1990). This is realized by changing the direction of the flow through the membrane. One of the main disadvantages of the given invention is that low molecular weight components of synthesis which inhibit operation of the system are not removed from the reactor during a long period. The time during which the feed solution passes repeatedly via the membrane is equal to the period when a total volume of feed solution passage via the membrane is equal to the complete volume of the reaction mixture. For this purpose N cycles are formed to create positive and negative pressure. Due to the pressure modulation the inhibiting products come back in the reactor together with a regular portion of the feed solution. Another disadvantage of this method is that upon formation of N cycles high molecular weight components of the cell-free system required for prolonged synthesis are intensively washed off the reaction mixture. Thus, repeated returning into the reactor of low molecular weight components inhibits operation of the system and removing from the reactor of high molecular weight components providing effective synthesis impose restrictions on operation of system.

The method (Choi. 1997) is known by which synthesis of polypeptides is carried out with removal of a target product in a dialysis mode of operation. For this purpose a membrane divides the reactor in two parts. The reaction mixture is placed on one side of the membrane and the feed solution on the other side. The reaction mixture is fastly circulating along the membrane surface in tangential direction. A disadvantage of the method is that due to a large pore size components of the system are removed together with the target products. Moreover, in spite of the fact that the dialysis process is quite effective because of the large pore size, its extent is not enough for operation of highly efficient cell-free systems.

The method (Alakhov et al., 1991) is known in which amino acids, ATP, GTP in an aqueous buffer are added to reactor during functioning of the system and low weight components such as AMP, GDP, Pi formed during synthesis and inhibit the system are removed through a membrane. To provide a more economical operation of the system, low molecular weight products are regenerated and come back into the reactor via the membrane. However from the description and the given figure it is not quite clear how low and high molecular weight components of the synthesis are removed from the reactor and in what way the buffer solution is regenerated after removal of the polypeptide. Taking into account the description of examples, low and high molecular weight components are removed from the reactor via the ultrafiltration membrane. The use of an ultrafiltration membrane is described in a number of publications (Spirin et al., 1988; Takanori et al., 1991; Spirin, 1992; Erdmann et al., 1994). A disadvantage of this method is the use of large sizes of the membrane cutoff. In this case high molecular weight components of systems necessary for synthesis are removed from the reactor together with target products. The volume of low molecular weight components is equal to that of the removed components which results in fast closing of the ultrafiltration membrane pores.

Methods of adding feed solution to the reaction zone and removing from it of reaction products for different types of membrane reactors are known in which the reaction zone is placed between two membranes (Matson et al., 1988; Wrasidlo et al., 1990; Dziewulski et al., 1992).

The method described in the patent (Alakhov et al., 1995) is the prototype of the method proposed herein. For synthesis of polypeptides in this invention the reaction mixture is placed between two flat membranes. The membranes differentiate flows of low molecular weight and high molecular weight components and divide the reactor into three zones: zone for input of feed solution, reaction zone, zone of product removal. The first rather weak flow is formed in the reaction zone. It ensures the reaction mixture movement along the internal part of porous barriers, through which they molecular weight components (including synthesized polypeptides) are removed. The second fast flow is formed in the zone of feed solution input. It ensures penetration of low molecular components via the membrane in the reaction system. The fast flow of low molecular weight components and the slow flow of high molecular components are achieved by creating a tangential flow along the external surface of the first porous barrier and dialysis process for adding feed solution in the zone of synthesis. If high molecular weight components are removed from the reactor, the size of cutoff is chosen from 50 to 100 kD (which is corroborated by example 7).

The speed of penetration of feed solution components to the reactor determined to a greater extent by the dialysis process is insufficient for maintenance of prolonged operation of highly effective cell-free systems.

Requirements to devices for scientific researches and for synthesis of polypeptides in preparative amounts are different. For synthesis of small amounts of polypeptides, from 100 to 200 $\mu$g, it is necessary to have a simple and cheap reactor which can ensure synthesis during 20–50 hours without application of expensive equipment and provides an opportunity to choose hand-operated or controlled speeds or flows.

During synthesis of polypeptides in preparative amounts, the device should control the process: operate speeds of flows inside the reactor and provides an opportunity for a prolonged (more than 50 hours) operation at the expense of active mixing or other action protecting from closing of membranes or hollow fibers, provide effective addition of the feed solution and expendable high molecular weight components to the reaction mixture and effective removal of low molecular weight components from the reactor which inhibit the synthesis.

The device (Mozayeny, 1995) is known which operates in the mode of continuous synthesis of peptides and is controlled by computer. The system includes a complicated and expensive equipment (an automatic sampler etc.).

Devices with one reactor from 1.0 ml. (Spirin et al., 1988) to 100.0 ml (Spirin, 1992) are known. Using the principle of dividing the entire reactor volume in several reactors of smaller volume it is possible to apply identical decisions to devices intended for synthesis of polypeptides in laboratory conditions and for prepartive synthesis. In this case routine technology of synthesis of polypeptides in small volumes of the reaction mixture from 50 $\mu$l up to 1–5 ml can be used in working with the volume up to 100–200 ml by scaling and increasing the amount of modules operating in parallel.

Devices for maintenance of synthesis in cells (Puchinger et al., 1980; Gebhard et al., 1997; Hu et al., 1997) using the principle of scaling the modules are known. In these devices inputs for supplying a feed solution and outputs for removal of products are connected in parallel for all N reactors. The known devices are designed for maintenance of cell growth and cannot be applied for synthesis of polypeptides, as each of N reaction modules serves to maintain speed, pressure and other parameters of flows of feed solutions and gases necessary for normal functioning of cells.

Known modules for bioreactors on the basis of hollow fibers (Gebhard et al., 1997; Hu et al., 1997) do not take into account the specifity of working with cell-free system. Fibers used in the reactors have the same size of a cutoff and their form reminds a beam placed in a cylinder. Therefore a significant part of the surfaces of hollow fibers contacts each other and reduces the working surface.

The device (Yagihashi et al., 1996) is known whose construction represents two layers of hollow fibers. Each layer consists of glued hollow fibers placed in parallel. Both layers of hollow fibers have the same size of a cutoff and a significant part of their surface is in contact.

The device (Pedersen et al., 1994) is known in which separate modules are single-layer constructions from hollow fibers with the same size of a cutoff.

However this technical decision has been developed for filtration of liquids and cannot be used in reactors for cell-free systems without essential modification in the design since it is intended for working with large volumes of liquid flows.

A large number of designs constructed on the basis of flat membranes is known. They also have disadvantages being intended basically for filtration or dialysis.

The device for synthesis of polypeptides in cell-free system is known (Mozayeny, 1995) whose structure includes two flat membranes. Originally this device (OMEGA TM) was intended for filtration and has a large void volume in the zones of product selection. The feed solution and high molecular weight components are added to the reactor through one input. This device is not intended for assembly in a general construction consisting of N modules.

The prototype of the proposed device for synthesis of polypeptides is the device described in the patent (Alakhov et al., 1985). For synthesis of polypeptides in a mode of product removal the device contains two porous barriers. These barriers can be executed as flat membranes or hollow fibers. The reaction mixture can be placed both from the external and internal sides of hollow fibers.

A disadvantage of the given device is that it contains porous barriers with the same size of a cutoff and provides for removal from the reactor of one flow consisting either of low molecular weight (the cutoff size of 7.5 kD) or high molecular weight (the cutoff size up to 100 kD) fractions.

SUMMARY OF THE INVENTION

The presence invention provides a method for synthesis polypeptides in a cell-free system by which products of synthesis are branched in a low molecular weight fraction and a fraction which contains high molecular weight components with the target polypeptide, the main part of the low molecular weight fraction is removed via at least one part of the second porous barrier, the ratio of the volume of the fractions of feed solution and expendable components to the volume of the fraction containing the target polypeptide is chosen, modes of supply of the feed solution and expendable components of the fractions are realized.

It is further object of the present invention to describe a methods for synthesis polypeptides in a cell-free system by which the low molecular weight fraction which consists of removed components including low molecular weight components of the reaction mixture and low molecular weight components of the synthesis is withdrawn from the reaction volume via at least one the second porous barrier only, the mode of supply of fractions of the feed solution and expendable components is realized.

It is therefor, also, an object of present invention to provide the method for obtaining polypeptides in which during the synthesis N cycles are formed, everyone of which consists of at least two steps, at the first step low molecular weight components of the feed solution are supplied to the reactor via the first porous barrier and the low molecular weight fraction with products of synthesis and components of the reaction mixture is removed via the second porous barrier, at the second step the supply and removal channels are switched and low molecular weight components of the feed solution are supplied via the second porous barrier, the low molecular weight fraction or the high molecular weight fraction containing products of synthesis and components of the reaction mixture is removed via the first porous barrier, the mode of supply of of fractions of the feed solution and expendable high molecular weight components is realized.

It is a further object of the present invention to describe a reactor which comprises at least one reactor volume, whose external surface contacts the external surface of the first and second porous barriers, the internal surface of the second porous barrier is connected to the zone of the inlet or outlet of low molecular weight flows, the internal side of the first porous barrier is connected to the zone of the inlet and outlet of low molecular weight flows and flows containing high molecular weight components with the target polypeptide.

BREEF DESCRIPTION OF DRAWINGS

The invention is explained by examples of performance with the references to the following figures.

THE LIST OF ABBREVIATIONS

F1 is the feed solution flow.
F10–F20 are flows of low molecular weight components of the reaction mixtures.
Ps are synthesized target polypeptides.
Pc are high molecular weight components of the system.
Rm is the reaction mixture.
Positions 100 are constructive elements of the reactor.
Positions 200 are liquid communications of the device.
Positions 300 are separate elements of the device: values, pumps, compartments for the eluate and compartments for storage of feed solution.
Position 400 is the controller block

DETAILED DESCRIPTION OF INVENTION

Generally the process can contain all of the following steps:
1. Prepare a reaction mixture on the basis of cell-free prokaryotic or eukaryotic lysates;
2. Prepare a feed solution and expendable components of high molecular weight fraction;
3. Determine the mode of operation of reactor, choose a type of the reactor module with the given types of porous barriers and install a device for synthesis whose structure includes, at least, one reactor module;
4. Place the reaction mixture in each of the reaction modules;
5. Depending on the mode of operation determine and set rates of the feed solution flow and the flow of expendable high molecular weight components through the reaction mixture and speeds of removal of low and high molecular weight products;
6. Carry out the synthesis providing the selected modes of operation, during the synthesis continuously or recurrently remove through a porous barrier the high molecular weight components or leave them in the reactor volume;
7. During the synthesis analyze the yield of the synthesized product, correct the parameters determining rates of feed solution flow and of the synthesized product, and supply or not supply expendable high molecular weight components.

FIGS. 1 (a–e) shows block diagrams explaining the principle of flow branching in a low molecular weight fraction and a fraction which contains high molecular weight components with target polypeptide for different modes of operations.

Figure 1A:
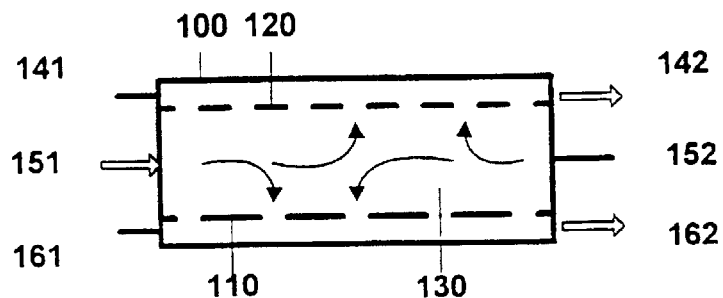
FIGS. 1(a–e) shows a scheme of principles of flow distribution for different modes of operations.

FIG. 1a shows a block diagram of flow branching inside the module in a mode of continuous removal of the target polypeptide. The reaction module contains case 100, within which three zones are formed using the first porous barrier 110 and second porous barrier 120. The reaction mixture Rm is supplied to reaction zone 130 before the beginning of the synthesis. The flow of feed solution F1 passes through input 151 in reaction zone 130 and displace high and low molecular weight components of the synthesis from the reaction mixture through the first and second porous barriers. The basic part of low molecular weight fraction passes through the second porous barrier 120 with a small size of a cutoff, forming flow F20 removed from the reactor volume through output 142.

Simultaneously high molecular weight components of synthesis Ps, components of cell-free system Pc and part of lower molecular weight components F10 which form the total flow PC+ Ps+ F10 are displaced from the reaction mixture through barrier 110 with a large size of a cutoff and through output 162. The ratio between the total volume of feed solution supplied to the reactor and the volume of the total flow Pc+ Ps+ F10 is chosen from 2 to 100. It is preferable that this ratio is from 10 to 50. A decrease in the rate of flow through the first barrier 110 diminishes formation of a layer of high molecular weight components above the surface of porous barrier 110 and diminishes the process of closing of membrane pores by high and low molecular weight components. The concentration of synthesized polypeptides Ps in the reaction mixture increases, thus promoting the next step of its clearing. The size of the cutoff of the first barrier 110 is chosen depending on the molecular weight of the synthesized polypeptide and its spatial organization.

Figure 1B:
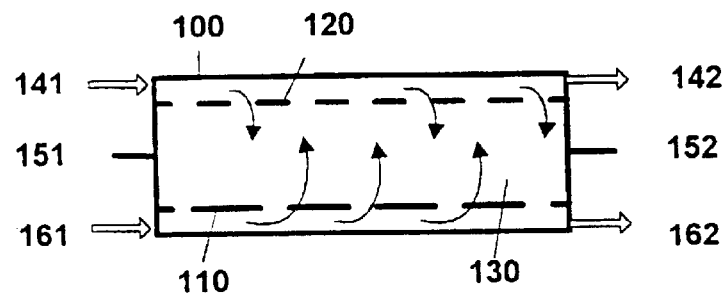

FIG. 1b shows a block diagram of flow branching of low and high molecular weight fractions inside the module in a mode of periodic removal of the target polypeptide. The reaction module contains case 100, inside which three zones are formed using the first porous barrier 110 and second porous barrier 120. Before the beginning of synthesis reaction mixture Rm is supplied inside reaction volume 130 through input 151. During the synthesis N cycles of flow input/removal through porous barriers 110 and 120 are formed. Each cycle consists of two steps. During the first step via input 161 the flow of feed solution F1 penetrates through the first barrier 110 inside inside reaction volume 130. The feed solution displaces low molecular weight components of reaction mixture and low molecular weight products of synthesis which form flow F20 from reaction mixture through porous barrier 120 and output 142. During the second step the direction of flow input/removal through porous barriers 110, 120 is changed. Through input 141 and second barrier 120 the flow of feed solution F2 penetrates inside zone 130. The pressure of feed solution forms a flow of low and high molecular weight components of the reaction mixture which passes through porous barrier 110 and output 162, and flow Pc+ Ps+ F10 is formed. Upon termination of the second step, the cycles comes to its end, the next cycle begins, or synthesis is terminated. The ratio between the total volume of the feed solution, supplied to the reactor during N cycles, to the volume of total flow Pc+ Ps+ F10 is selected from 2 to 100. It is preferable that this ratio varies from 10 to 50.

A decrease in the rate of flow through the first barrier 110 diminishes formation of a layer of high molecular weight components above the surface of porous barrier 110 and diminishes the process of closing of membrane pores by high and low molecular weight components. The concentration of synthesized polypeptides Ps in the reaction mixture increases, thus promoting the next step of its clearing. The size of the cutoff of the first barrier 110 is chosen depending on the molecular weight of the synthesized polypeptide and its spatial organization. The first and second porous barriers are cleaned by changing directions of flows through porous barriers. Duration of a cycle and the temporary ratios between duration of the first and second steps are maintained constant during all synthesis, or are changed depending on conditions of the synthesis. If the synthesis goes actively and the concentration of polypeptides in the reaction mixture quickly grows, to prevent closing of the porous membrane the duration of each cycle is reduced which automatically results in more frequent clearing of the pores.

Figure 1C:
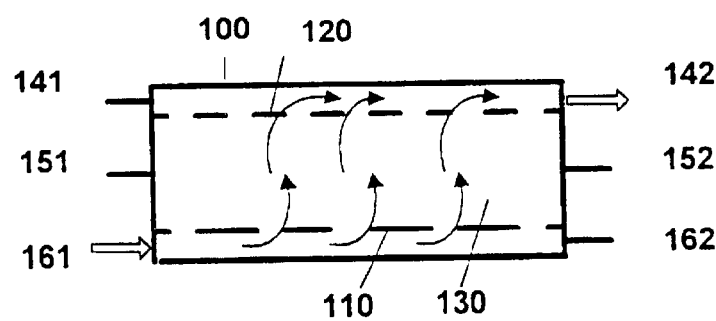

FIG. 1c shows a scheme of flow directions in the mode of operation without product selection. During the synthesis all high molecular weight components remain inside the reaction mixture. The feed solution flow F1 enters through the first porous barrier 110, which has pore size up to 1000 kD. The flow of low molecular weight pounds F10, which inhibiting the cell-free system, is removed via the second porous barrier 120. The first porous barrier is an allocator flow F1 and provides uniform input of the feed solution to all points of the reaction mixture.

Figure 1D:
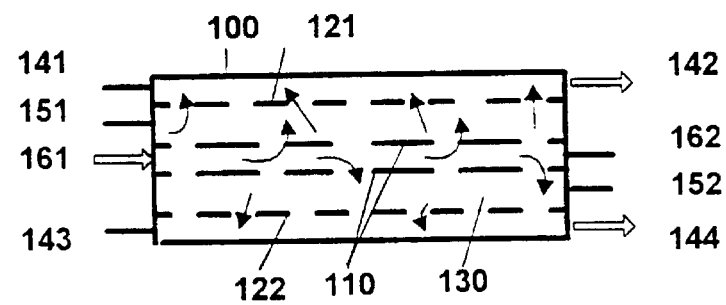

FIG. 1d shows a scheme directions of flows in the mode of operation without product selection for reactor module which have at least one the first porous barrier and two parts of second porous barrier. During the synthesis feed solution flow F1 and/or part of expenable components with high molecular weight penetrate through porous of the first barrier 110, which has pore size up to 1000 kD This porous barrier is an allocator flow F1 and provides uniform input of the feed solution to all points of the reaction mixture. The flow of low molecular weight products F10 which inhibiting the cell-free system is removed via the two parts of second ports barrier 121–122, which has pore size up to 30 kD.

Figure 1E:
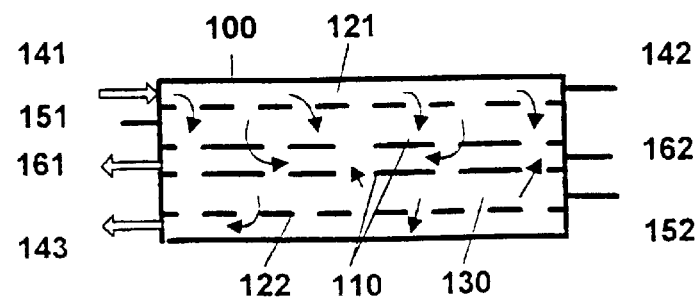

FIG. 1e shows a scheme directions of flow in the mode of operation with product selection for reactor module which have at least one the first porous barrier and two parts of second porous barrier. During the synthesis all high molecular weight components including target polypeptides is removed from reaction mixture via the first porous barrier 110, which has pore size up to 100 kD The feed solution flow F1 enters through the one part of the second porous barrier 121, which has pore size up to 30 kD. The porous barrier is an allocator flow F1 and provides uniform input of the feed solution to all points of the reaction mixture. The flow of low molecular weight products F10 which inhibit the cell-free system is removed via the another part of second porous barrier 122, which has pore size up to 30 kD.

For realization of the considered method several constructions of the reactor module are offered. The device can provide synthesis of products in different modes. The module should allow for several conditions:

1. In each point of the reactor at least two processes should be carried out simultaneously: (a) input of feed solution, (b) removal of low molecular weight components which inhibit the synthesis.
2. Input of feed solution and removal of low molecular weight components of products should be carried out in the time during which the synthesis drops below the admissible magnitude.
3. The device should allow effective clearing of the porous membranes or hollow fibers and contain a minimum of void volumes in the liquid communications for input/removal of lower/higher molecular weight components/products of synthesis.

For realization of the first and second conditions, a reactor module in which whatever thin layers of the reaction mixture can be formed is most preferable. The thickness of a layer is chosen from 0.1 mm up to 10 mm provided that at the given areas of the first and second porous barriers and chosen sizes of their cutoff the average speed of feed solution input in the reactor ensures input of the feed solution components in the most remote points of the reaction mixture in time during which the feed solution concentration in the remote points drops to the admissible level, and the concentration of low molecular weight components inhibiting the synthesis does not exceed this level.

With devices working in the mode in which the feed solution or/and high molecular weight components move directly to the reactor through at least one input it is preferable to use additional mixing in the reactor. Such mixing can be performed by a rotating magnetic stir bar or transfer of the reaction mixture via the external closed loop or other methods.

For devices in which a thin layer of the reaction mixture is formed, a module with a separator between layers of porous barriers is most preferable. A different type of separator can be used and may be selected from the group of a single or multiple layer, capillary materials, a combination of layers of capillary material and porous particles, a single or multiple thin layer sheets from organic, synthetic or ceramic material, metals or their compositions and porous particle between layers. Another type of separators may be of hollow-fibers. Filters widely used for filtration and made of different type of cellulose of synthetic polymeric materials, metals and ceramics may be also used as separators. The role of layered capillary materials is not only to divide two porous barriers, but also to increase the area on which binding of molecules occurs that increases the speed of reactions connected with the synthesis (Alberts et al., 1986).

It is more expedient to use immobilized porous particles plated on the surface of layered capillary structures. The diameter of fibers is taken from 0.1 up to 0.001 depending on the diameter of hollow fibers. Particles of porous material from 10 microns to 0.1 mm are layered on the surface of fibers. In case hollow fibers are used as the first and/or second porous barriers, the fibers of layered materials are accommodated either along hollow fibers occupying the space between them, or at an angle to the central axes of hollow fibers not exceeding 90 degrees (i.e. Across the layers of hollows fibers). The materials of which porous particles can be made include (Choi et al., 1997): polymeric materials (cellulose, gelatin, gollagen), metal compounds and inorganic oxides (aluminum, silica, titanium, zirconium, molybden, vanadium, cobalt) and various zeolites. Porous particles can be used as granules (Ovodov et al., 1995) on the basis of negatively charged polysaccharides and positively charged polymers which form polyelectrolyte complexes with polysaccharides. Such complexes can be formed, for example, by sodium alginate and poly-L-lysine, sodium alginate and chitosane, pectin and polyimine, pectin and chitosane. The materials of which the porous particles are made may include sorbents used in chromatography, affinity sorbents can be also used to sreate a porous medium in reaction volume and to isolate the target polypeptide from the reaction system after synthesis. Chemical activity and possibility to inhibit synthesis is restricted for some porous material.

When a cell-free system is immobilized in granules (Ovodov et al., 1995; Alakhov et al., 1995), the most preferable design is the reactor module allowing to plate several layers of microganule with immobilized cell-free system on the surface of the first porous barrier so that they fill the whole reactor. In this case a rather thin layer of microgranules is formed determined by the height of the reactor, which allows to supply feed solution to the zone of synthesis and to remove the low and high molecular weight components at the optimal speed.

FIGS. 2a–e shows variants of thin layer formation inside the reactor module when flat semipermeable membranes and hollow fibers or their combinations are used as porous barriers.

Figure 2A:
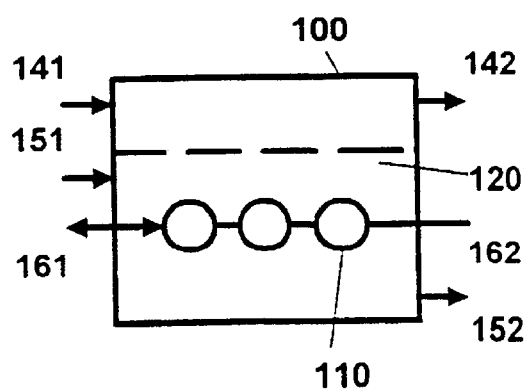
FIGS. 2(a–f) shows block diagrams of modules based on the declared principle.

FIG. 2a shows the case when thin layers of the reaction mixtureare formed between the flat surface of membrane 120 and cylindrical surfaces of hollow fibers that play the role of the first barrier 110 and has the form of at least one layer of parallel hollow fibers. The amount of hollow fibers depends on the cutoff size of the first and second barriers as well as on the diameter of hollow fibers determining their area. If the ratio of the cutoff sizes of the first and second barriers is from 3 up to 10, the area of the first barrier is taken from 0.2 to 1.0 of that of the second barrier.

Figure 2C:
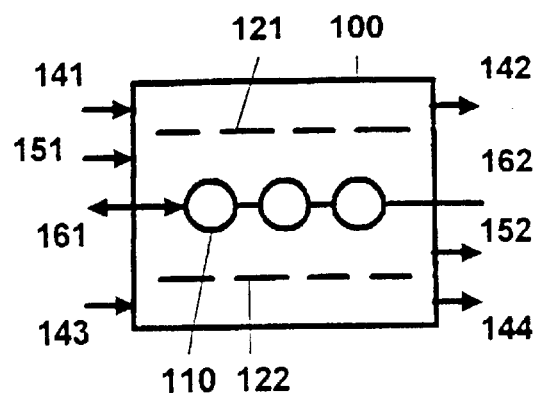
Figure 2B:
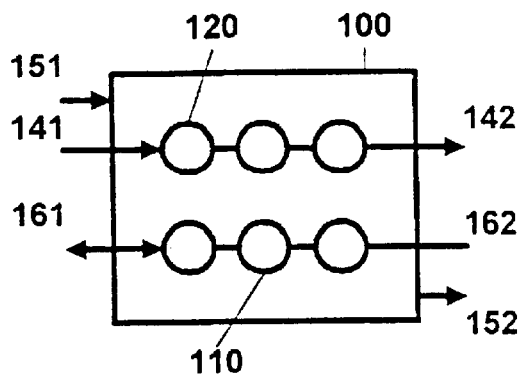

FIG. 2b shows the case when the reaction layer is formed between two layers of hollow fibers functioning as the first barrier 110 and second barrier 120. In every layer hollow fibers are placed parallel to each other. The central axes of hollow fibers placed in different layers are either parallel or are at an angle from 70 degrees to 110 degrees. The ratio of the amount of hollow fibers in the first layer to the amount of hollow fibers in the second layer is taken to be from 1 to 0.1 depending on the ratio of the cutoff sizes. Most preferable is such a design of this module when the total volume of reactors is assembled from several modules. In this case the modules are located so that layers of hollow fibers from the first and second barriers are alternated, thus allowing to distribute uniformly the flows of low and high molecular weight components via the whole volume of the reactor.

When the synthesis is carried out with cell-free systems whose efficiency is from 2 to 4 times higher than the known level in 100–200 Mg (for example if concentrate reaction mixture is used), it is necessary to improve the feed solution input to the reactor and decrease the influence of closing of membrane pores by products of synthesis. To ensure uniform distribution of the feed solution over the entire volume of the reaction mixture and to lower the closing of the cutoff, a module with three porous barriers is used. In this case a layer of hollow fibers parallel to each other is used as the first porous barrier. This layer is placed in the middle part of the module between two porous barriers, which function as the second porous barrier with a small size of the cutoff. In this variant the area of the second porous barrier is doubled, that positively influences the removal of low molecular weight products inhibiting the synthesis. This permits to lower the pressure upon the formation of the flow or removed low molecular weight products.

FIG. 2c shows a reactor module in which the reaction layer is placed between two flat membranes with a layer of hollow fibers between the latter. This design of the module is more preferable when one reactor unit is formed from several modules. In this case zones for removal of low molecular weight components are joined together and the number and length of liquid communications is reduced.

Figure 2D:
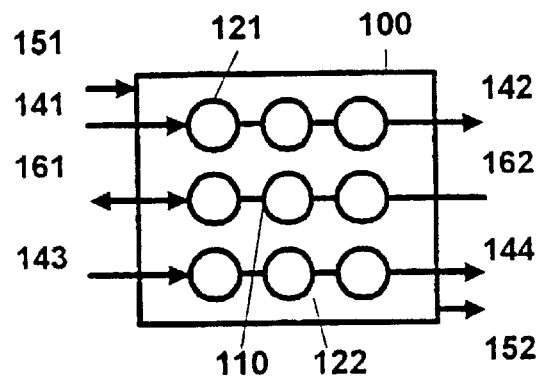

FIG. 2d shows a design of the module from three layers of hollow fibers. Hollow fibers in each layer are placed parallel to each other. The middle layer is placed in such a manner that the central axes of its hollow fibers are at an angle from 70 up to 110 degrees relative to the central axes of the other layers or are parallel. It is preferable to use perpendicular allocation of the axes. In this case the area of contacting zones between the surfaces of the first, second and third layers of hollow fibers is reduced if no grids or porous layered materials are placed between the layers. The ratio of the amount of hollow fibers in the first and third layers to the amount of hollow fibers in the second layer is accepted from 1 up to 0.1 depending on the ratio of the cutoff sizes of the hollow fibers.

Figure 2E:
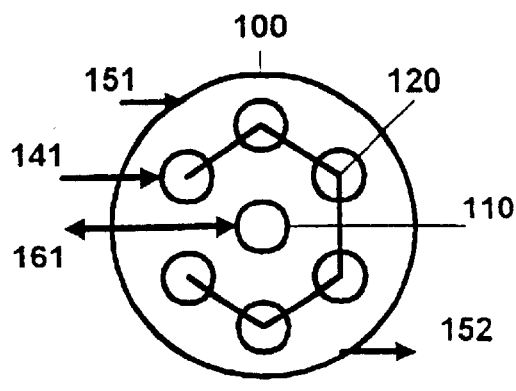
Figure 2F:
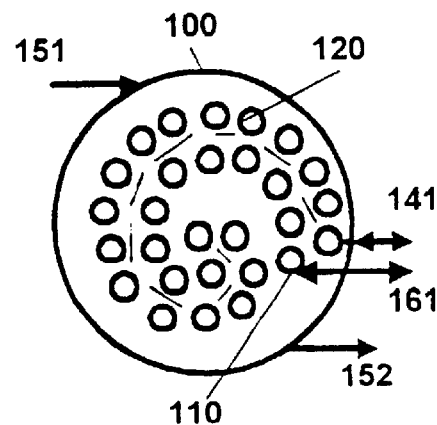
Figure 3:
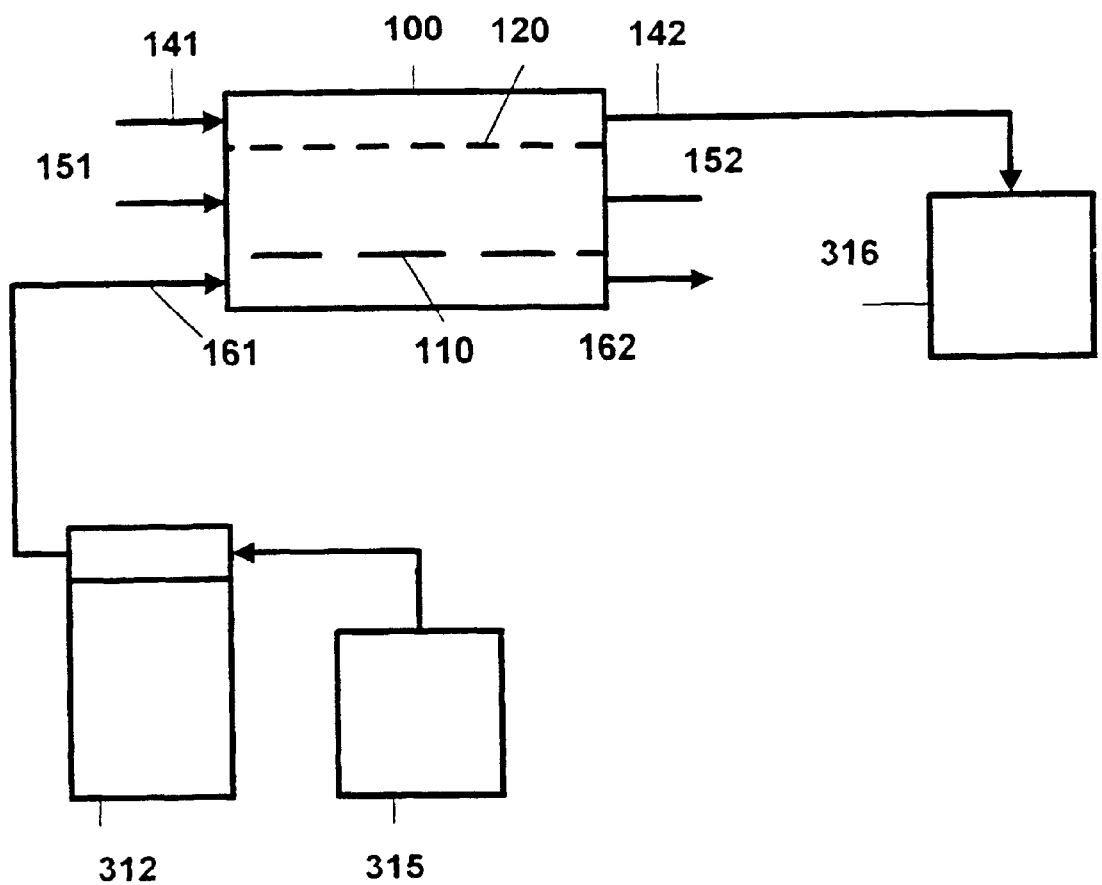
FIG. 3 shows a block diagram of the device for synthesis in a mode without removal of the target polypeptide.
Figure 4:
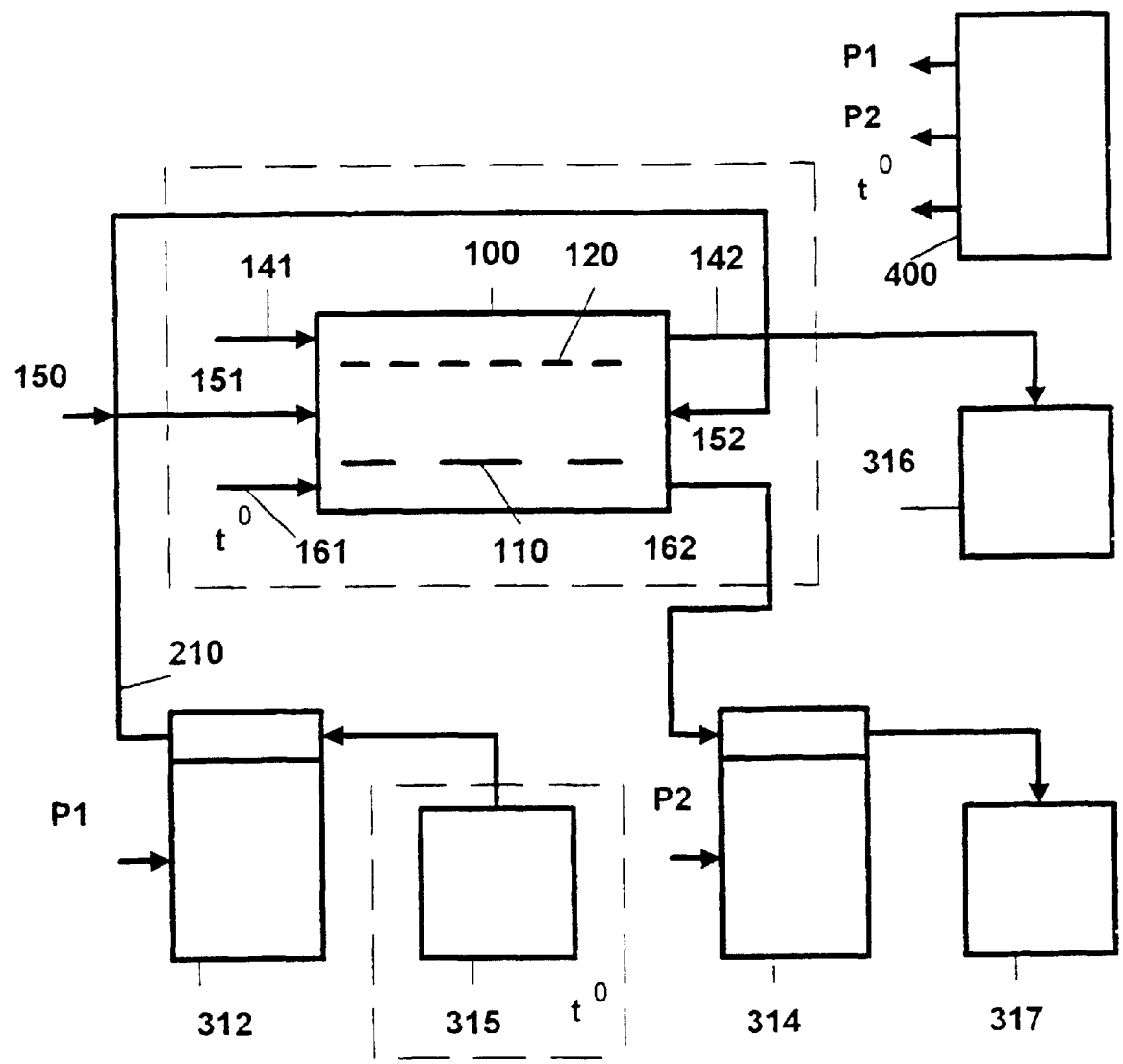
FIG. 4 shows a block diagram of the device for synthesis in a mode of removal of the target polypeptide.

In the above versions of the reactor modules the shape of sheet membranes and sheets consisting of one-layer hollow fibres can be either square or round. FIG. 2e and FIG. 2f show reactor modules having the form of cylinders in which the reaction volume has the shape of (i) a helix or (ii) a cylinder.

A difference from the known designs is the formation of a two-layer construction with different cutoff sizes and diameters of hollow fibers used. FIG. 2e represents a module in which the central element made of a hollow fiber plays the role of the first porous barrier with a cutoff up to 100 kD. It is coated by fibrous material to prevent direct contact of the first and second porous barriers. Then hollow fibers of the second porous barrier are placed around the central element. The amount of hollow fibers in the second porous barrier and the area of their surface should exceed those of the first barrier by no less than 5–10 times. Then a beam of hollow fibers is placed in a cover which has an input and output for the reaction mixture and its end faces are glued as described by Yagihashi et al. (1996), forming an output for one porous barrier from one side of the cylindrical cover and an output for the other porous barrier from the opposite side. FIG. 2*f* shows a two-layer design in which porous or layered material is placed between the two layers. The preliminary prepared sheets of their single-layer constructions playing the role of the first and second barriers are curled and placed inside the cylindrical cover with input 151 to the reactor. Internal outputs of each hollow fiber of the first barrier are united in a common output 161 from one part of the cylinder, and internal outputs of each hollow fiber of the second barrier are united in a common output on the opposite part of the cylinder.

The form of the reaction module is chosen depending on conditions providing for the following: washing the reaction zone, accessible input of the reaction mixture to the reaction zone without formation of air zones, maintenance of minimal volumes in the zones of input/removal of feed solution and low and high molecular weight components of synthesis. Of great importance is the simplicity of assembly and disassembly of the module for clearing the cutoffs of membranes and hollow fibers. An assembly construction (when at least one module is used) is formed by installation of membranes, hermetic layers, top and bottom covers into the frame of the module. It is preferable that one porous barrier is pasted to the frame and the other barrier is removable. This provides an opportunity of easy access to the reaction zone and enables to determine defects of membranes or hollow fibers that can appear during operation.

It is preferable to use mould materials which can perform two functions, i.e. be a support for porous barriers and hermetically seal the layers. Such materials can be silicon hermetic or other synthetic materials with good adhesion to polymeric materials from which the membrane and hollow fibers are made. The properties of these materials should provide repeated restoration of the form after elimination of squeezing effort.

Porous barriers can be made of different materials. Nevertheless most preferable are those which can allow regeneration and purification of pores after termination of synthesis without disassembly of the reactor or at its disassembly and subsequent assembly. Clearing of many types of membranes and hollow fibers are described in detail in technical catalogues of firms (Operating Guide, 1997).

Cutoffs of the first porous barrier 110 are chosen from 30 up to 300 kD. For most polypeptides with molecular weight of 20–40 kD it is more preferable to use cutoffs of 50–100 kD. Cutoffs of the second barrier 120 are taken from 1 up to 30 kD depending on the molecular weight of synthesized polypeptides and conditions of passage through this barrier of the given flow of low molecular weight components. For synthesis of polypeptides with molecular weight of 20–40 kD it is preferable to use cutoffs of barrier 120 from 10 to 12 kD.

FIG. 3–6 show examples of schemes of devices for different modes of operation.

The most simple device for synthesis of polypeptides (FIG. 3) uses a mode without removal of high molecular weight components from the reaction mixture. It consists of at least one reaction module 100, pump 312 and capacities for the feed solution 315 and waste compartment 316 for low molecular weight components. The reaction mixture enters the reactor through input 151. By pump 312 the feed solution is supplied through input 161 and first barrier 110 to the reaction mixture. Low molecular weight components inhibiting operation of the system, are removed from the reactor via second porous barrier 120 and output 142 and come to waste compartment 316.

In another example when the experimenter chooses a mode of continuous removal of the product, the flows are distributed as follows. At the first step installation of the system for polypeptide synthesis (FIG. 4) is done using reactor 100 which consists of at least one reaction module with two porous barriers, pumps 312 and 314, capacities for storage of feed solution 315, waste fraction 316 and high molecular weight (with the targed polypeptide) fraction 317. The device works in the following way. The reaction mixture enters the reaction zone of the module via liquid communication input 150, the feed solution from capacity 315 is supplied to the next input 151 of this module through liquid communications 210 and pump 312 and is distributed over the entire volume of the reactor, thus displacing products of synthesis. High molecular weight products of synthesis, including synthesized polypeptides, penetrate through the first porous barrier 110 and are removed from the reactor via pump 314 with a given speed. Due to the pressure created by pump 312 low molecular weight components are removed through the second porous barrier 120 and output 142, which is connected directly to waste compartment 316. The size of the cutoff of the first and second porous barriers as well as the speed of pumps depend on conditions of the synthesis. The design of the module used for this mode requires the presence of at least two porous barriers in the form of two flat membranes (FIG. 1*a*) or two layers of hollow fibers (FIGS. 2*b,e,f*), or a combination when one of barriers is a membrane and the other consists of hollow fibers (FIG. 2*a*).

Figure 5:
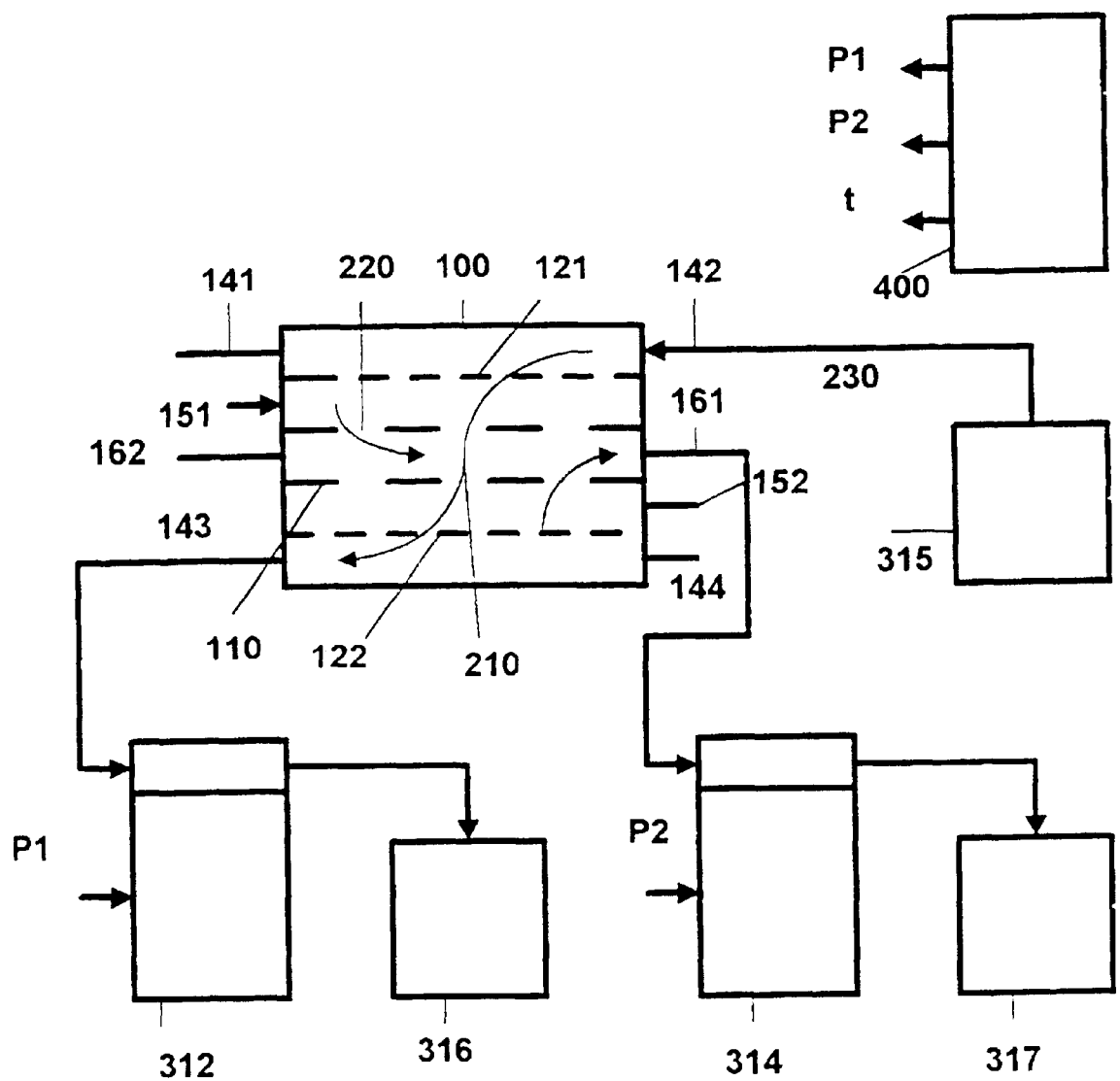
FIG. 5 shows a block diagram of the device for synthesis in a mode of removal of the target polypeptide with a three porous barriers in module.
Figure 6:
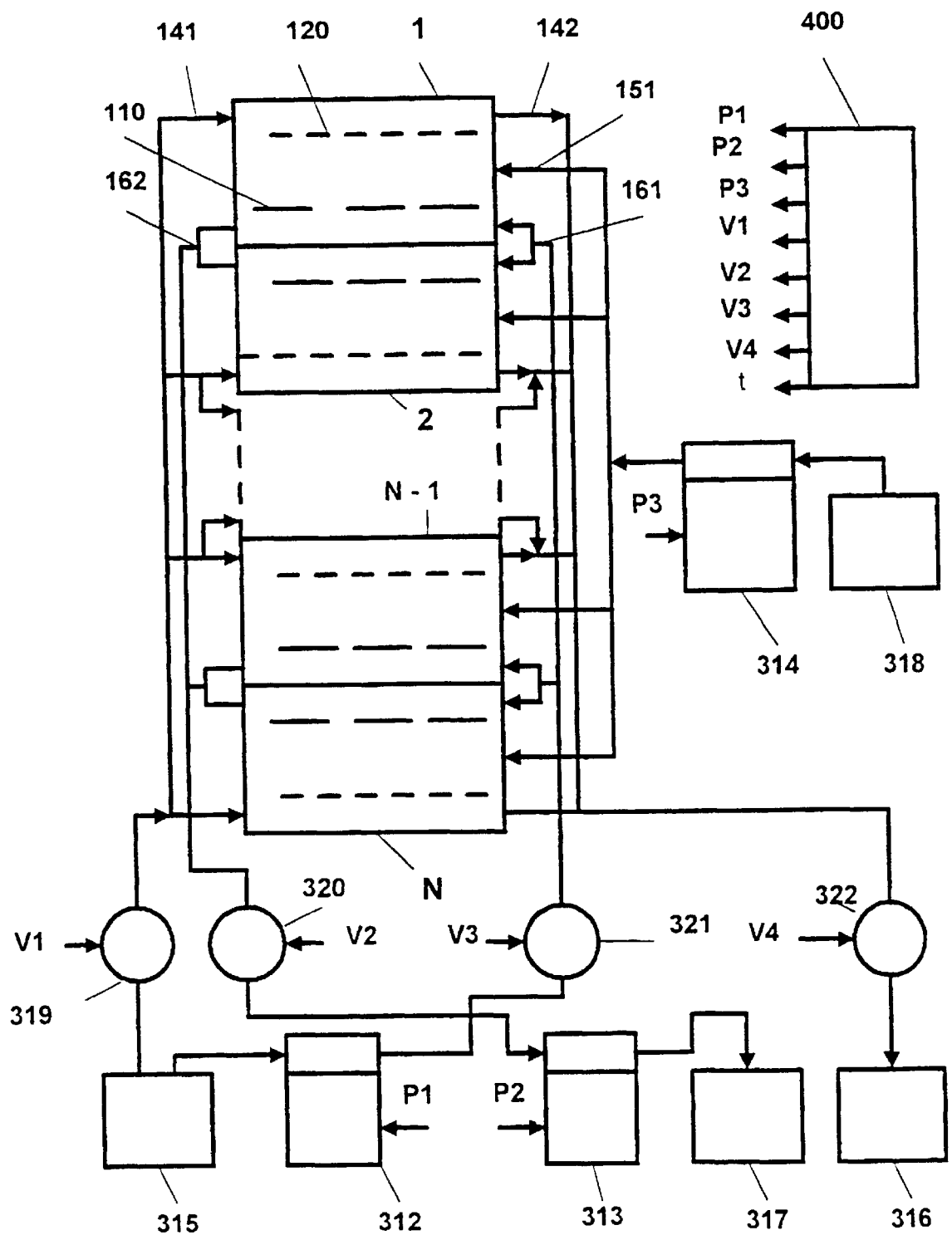
FIG. 6 shows a block diagram of the device for synthesis in a mode with periodic removal of the target polypeptide.

When conditions of synthesis require a uniform input of the feed solution in all points of the reaction zone, a device with reactor modules consisting of three porous barriers is used. Such a device is shown in FIG. 5. The reaction mixture enters the reactor through input 151. The flow of feed solution 210 enters the reactor from capacity 315 via liquid communications 230, input 142 and porous barrier 121. The type of a porous barrier depends on conditions of synthesis. It is more expedient that the first barrier 110 is made from hollow fibers and two second barriers 121 and 122 are formed from flat membranes or hollow fibers. Through porous barrier 121 the feed solution penetrates into the reactor on the thin layer of the reaction mixture due to negative pressure in the second part of porous barrier 122. The negative pressure is created by pump 312 whose input is connected to output 143 connected with internal surfaces of the second porous barrier 122. The output of pump 312 is connected to waste compartment 316 for low molecular weight components. High molecular weight components of products are removed through the first barrier 110 which is made from hollow fibers placed in regular intervals over the thin layer of the reaction mixture. The internal part of hollow fibers is incorporated in a common output 161, which is connected to the input of pump 314, whose output is connected to collector 317 for high molecular weight components.

When it is required to carry out preparative synthesis and the reaction mixture volume is from 1 ml to 500 ml, a parallel connection of N reaction modules is used. The scheme of a device using a parallel connection of N modules is shown on FIG. 6. This example is based on periodic removal of the product when high molecular weight components of target products are removed partially at the end of each cycle with simultaneous automated clearing of pores of the first and second porous barriers. Reactor 100 is filled with the reaction mixture through input 151. In the initial condition valves V3 and V4 are open whereas valves V1 and V2 are closed. At the first step of a cycle the feed solution moves from capacity 315 through pump 312 and valve V3 simultaneously to all N inputs 161.

Then the feed solution passes through internal apertures of hollow fibers or across the internal surface of the membrane from which the first porous barrier 110 is formed. Through pores of the first porous barrier 110 the feed solution penetrates readily to volume with reaction system. Low molecular weight components of the synthesis pass through the second porous barrier 120 with a small cutoff and are removed through N outputs 142 and open valve V4 in waste compartment 316 for the low molecular weight components. On termination of the first step of a cycle and beginning of the second step valves V3 and V4 are closed and valves V1 and V2 open. Pump 313 creates negative pressure in the channel connected to valve V2. Under negative pressure, high molecular weight components of synthesis including target polypeptide leave the reactor through the first barrier 110 and come to fraction collector 317 via output 161, valve V2 and pump 313. At the same time the feed solution comes to the reactor from capacity 315, input 141 and second barrier 120 under the action of negative pressure created by pump 313. The flow of the feed solution via the second porous barrier 120 at the second step of the cycle has a different direction than that low molecular weight components formed at the first step of cycles. Therefore pores of the second barrier 120 which could be closed at the first step of a cycle open during the second step of the cycle and hydraulic resistance of second barrier 120 is restored. After termination of the second step of a cycle its first step is formed. The flow of high molecular weight components via the first porous barrier 110 is stopped. At the first step of a cycle the flow via first porous barriers changes its direction and pores of the first barrier 110 which could be closed at the second step of a cycle by high molecular weight components open and hydraulic resistance of the first barrier 110 is restored. A cycle terminates with the end of the second step, and the control device monitors switching of valves thus giving impetus for the formation of the first step of the cycle. The ratio of the feed solution volume entering the reactor and the volume of the fraction of high molecular weight components removed from the reactor is changed by varying temporary ratios of the times of the first and second steps of a cycle and changing its total duration.

It is known (Kim et al., 1996) that by raising the concentration of lysate it is possible to increase the yield of synthesized polypeptides. The data reported in the cited art relate to a batch type reaction, when the products inhibiting the cell-free system are not removed from the reaction mixture. This reduces the yield of the synthesized product. It is possible to raise the yield of polypeptides by removing low molecular weight components of products from the reactor and supplying high molecular weight components which lose their activity during synthesis. Experiments have shown that one removal of low and high molecular weight components of products from the reactor it is possible to add in the reactor not only the feed solution but such components of lysate as ribosomes fraction, extracts (S30, S100 and others), polymerase (T7, T5, SP6 and others), plasmids, tRNA, enzymes or their combinations.

The proposed construction of a reactor module allows to add the feed solution and lysate components to the reactor in the following ways: (a) the whole volume of feed solution is supplied via the reactor input; (b) the whole volume of feed solution is supplied via the first barrier; (c) part of the feed solution is supplied via the first barrier and the other part via the reactor input; (d) part of the feed solution is supplied via the first barrier during the first step of a cycle and the other part is supplied via the second barrier during the second step of the cycle; (e) the whole volume of lysate components is supplied via the reactor input together with the whole volume of the feed solution or its part; (f) the biggest components of lysate (ribosomes and others) and part of the feed solution are supplied via the input of the reaction zone while small components of lysate and part of the feed solution are supplied in the reaction zone via the pores of at least one barrier. As an example FIG. 5 shows the case when pump 314 can supply high molecular weight components of lysate from capacity 318 as monitored by the controller.

Reactor modules are thermostated from 20° C. to 40° C. (the usual range is from 25° C. to 37° C.). It is preferable if the feed solution temperature is from +2° C. to +7° C. The pumps are hand-operated or monitored by controller block 400. This block should provide programming of modes of operation. The automated systems on the basis of computers developed by Roche Diagnostic Boehringer Mannheim have been shown to yield very good (Simonenko, 1998). The controller block allows to adjust the duration of cycles and the ratio of two steps in a cycle.

At installation, for example, of pressures gauges it is possible to trace the change of pressure in the liquids circuits by the level of closing of the cutoff and to change conditions of the process in due time.

The proposed method of flow branching provides synthesis of polypeptide in a cell-free prokaryotic and eukaryotic extracts with high speed during tens of hours with removal of functionality active products. As an example the synthesis of fibrous GFP is given. The synthesis was carried out with the help of a device whose block diagram is given in FIG. 4. Ultrafiltration membrane with the cutoff from 50 kD to 10 kD were used as the first and second porous barriers in the reactor module. The volume of the reaction zone was 400 $\mu$l.

In the given example the method of preparative synthesis of polypeptides in the conjugated system of transcription/translation is used (Baranov et al., 1989). Most frequently estimation of the efficiency of cell-free systems is made by measuring the amount of radioactive amino acid contained in the synthesized polypeptides (Alakhov et al., 1991). As an alternative method, specific properties of polypeptides such as fluorescence (Kolb et al., 1996; Cramer et al., 1996) are employed.

The S30 extract from *E. coli* is prepared by a modified method (Zubay, 1973) as follows. *E. coli* A19 cells are grown to optical density of the culture—0.8 at the wavelength of 582 nm. The cells are collected by centrifugation. The obtained biomass is washed twice being resuspended in buffer A: 10 mM Tris-Ac pH 8.2, 14 mM $Mg(OAc)_2$, 60 mM KCl, 1 mM dithiothreitol by centrifugation for 30 min at 10,000 g. The washed biomass is resuspended in buffer A with the ratio 4 volumes of the buffer to 1 volume of cells. The obtained suspension is destroyed by the French-press at the pressure drop of 1600 bars. Destruction is carried out at +4° C. Commercial protease inhibitors in concentrations recommended by their manufacturers are added to the obtained cell extract, and the mixture is centrifuged for 30 min at 30,000 g. Eliminating agitation, $\frac{2}{3}$ of supernatant volume is collected. The volume collected is centrifuged once again for 30 min at 30,000 g. Eliminating agitation, $\frac{2}{3}$ of the supernatant volume is collected. All procedures are carried out at +4° C. Buffer B containing 750 mM Tris-Ac pH 8.2, 21 mM (OAc)$_2$, 7.5 mM dithiothreitol, 6 mM ATP, 500 mM acetylphosphate, 500 $\mu$M of each of 20 amino acids. The obtained solution is incubated at 37° C. during 80 min. After termination of incubation the extract is dialyzed against buffer C: 10 mM Tris-Ac pH 8.2, 14 mM Mg (OAc)$_2$, 60 mM KOAc, 0.5 mM dithiothreitol during 16 h. The dialysis is carried out at +4° C. in a 500-fold volume of buffer C with two changes. After termination of dialysis the resulting volume is centrifuged for 30 min at 10,000 g, selected in aliquots and frozen in liquid nitrogen for subsequent storage at −70° C.

The coupled system of transcription/translation is prepared as follows.

1 ml of the reaction mixture contains 200–400 $\mu$l of the S30 extract from *E. coli*, 0.1–0.5 mg of the total tRNA from *E. coli* 0.01–0.03 of the plasmid superhelical DNA, 2000–3000 U DNA-dependent RNA from polymerase of bacteriophage T7, 10–50 U of ribonuclease inhibitor of human placenta in buffer D: 50–100 mM HEPES-KOH, or 50–100 mM Tris-Ac, or 50–100 mM TES-KOH, or 50–100 mM MOPS-KOH, or 50–100 mM BES-KOH, pH 7.0–7.6. To the same reaction mixture we add low molecular weight compounds containing 10–20 mM Mg (OAc)$_2$ or MgCl$_2$, 120–230 mM KOAc or K-L-glutamate, 1.0–2.0 mM ATP, 1.0–2.0 mM GTP, 0.8–1.5 mM CTP, 0.8–1.5 mM UTP, 25–40 mM acetylphosphate, 40 $\mu$g/ml leucovorin, 1 mM dithiothreitol, 4% glycerol, 0.02% NaN$_3$ and 150–250 $\mu$M of each of 19 amino acids excepting the one with which control synthesis in an aliquot of a fixed volume is carried out.

The prepared transcription/translation system is divided in two unequal volumes. The smaller volume (30–50 $\mu$l) is placed in microtube and the amino acid containing a radioactive label is added to it. Then aliquots of 5–10 $\mu$l are taken from the microtube to estimate the kinetics of the synthesis in a fixed volume. The amount of synthesized polypeptides is determined by aliquot precipitation on a glass fibrous filter with trichloracetic acid, with particles irradiated by the isotope being counted in a liquid scintillator. Then the lacking amino acid in the concentration of 150–250 $\mu$M is added to the remaining volume and after slight and cautious stirring is placed in the reaction cell. Synthesis is carried out at 26 to 37° C. passing the feed solution through the reaction mixture to the reactor module.

The feed solution is prepared as follows.

1 ml of the feed solution contains the following low molecular weight substances: 10–20 mM Mg (OAc)$_2$ or MgCl$_2$, 120–230 mM KOAc or K-L-glutamate, 1.0–2.0 mM ATP, 1.0–2.0 mM GTP, 0.8–1.5 mM CTP, 0.8–1.5 mM UTP, 25–40 mM acetylphosphate, 40 $\mu$g/ml leucovorin, 1 mM dithiothreitol, 4% glycerol, 0.02% NaN$_3$ and 150–250 $\mu$M of each of 20 amino acids in buffer D. Buffer D contains 50–100 mM HEPES-KOH, or 50–100 mM TES-KOH, or 50–100 mM MOPS-KOH, or 50–100 mM BES-KOH, pH 7.0–7.6. To the same solution we add 200–400 $\mu$l of buffer C containing 10 mM Tris-Ac pH 8.2, 14 mM Mg (OAc)$_2$, 60 mM KOAc, 0.5 mM dithiothreitol.

EXAMPLE 1

The coupled transcription/translation of green fluorescent protein (GFP) of coelenterate bacterium *Aequoria victoria* from a DNA template containing a GFP gene, in continuous cell-free from *E. coli*, with branched flows.

A plasmid DNA containing a mutant gene of GFP and nucleotide sequences of a ribosome-binding site and a promoter of the DNA-dependent RNA-polymerase of bacteriophage T7 is used as a template.

The coupled transcription/translation system is prepared as follows.

1 ml of the reaction mixture containing 200–400 $\mu$l of the S30 extract from *E. coli*, 0.1–0.5 ml of the total *E. coli* tRNA preparation, 0.01–0.03 mg of plasmid superhelical DNA, 2000–3000 U of DNA-dependent RNA polymerase of bacteriophage T7, 10–50 U ribonuclease of human placenta inhibitor in buffer E (100 mM HEPES-KOH, pH 7.6). To the same reaction mixture we add low molecular weight substances containing 12 mM Mg(OAc)$_2$, 220 mM KOAc, 1.2 mM ATP, 1.0 mM GTP, 0.8 mM CTP, 0.8 mM UTP, 30 mM acetylphosphate, 40 $\mu$g/ml of leucovorin, 1 m dithiothreitol, 4% glycerol, 0.02% NaN$_3$ and 160 $\mu$M of each of 19 amino acids excepting leucine.

The prepared transcription/translation system is divided in two unequal volumes. The smaller volume (30–50 $\mu$l) is placed in a microtube and [$^{14}$C]-L-leucine with specific radio-activity 38 mCu/mmol and 100 $\mu$M concentration is added to it. Then aliquots of 5–10 $\mu$l are selected from the microtube to estimate the kinetics of synthesis in a fixed volume. The amount of the synthesized polypeptide is determined by aliquot precipitation on the glass fibrous filter by trichloroacetic acid with subsequent estimation of irradiated particles in a liquid scintillation counter. Leucine in 160 $\mu$M concentration is added to the remainder volume and after sight and cautious mixing the preparation is placed in a reaction cell.

Figure 7:
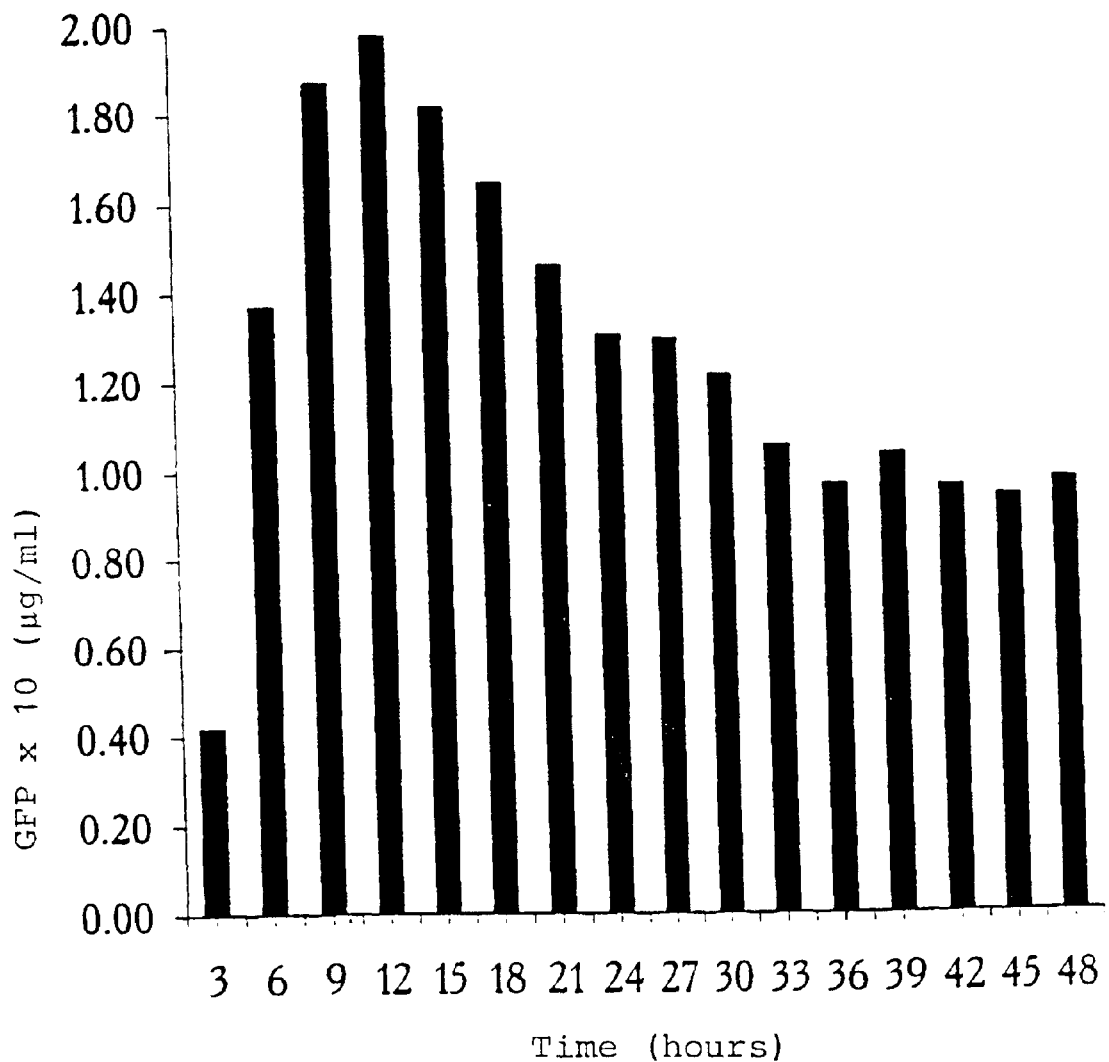
FIG. 7 shows a histogram reflecting the amount of GFP in the fractions in accordance with the description in Example 1.
Figure 8:
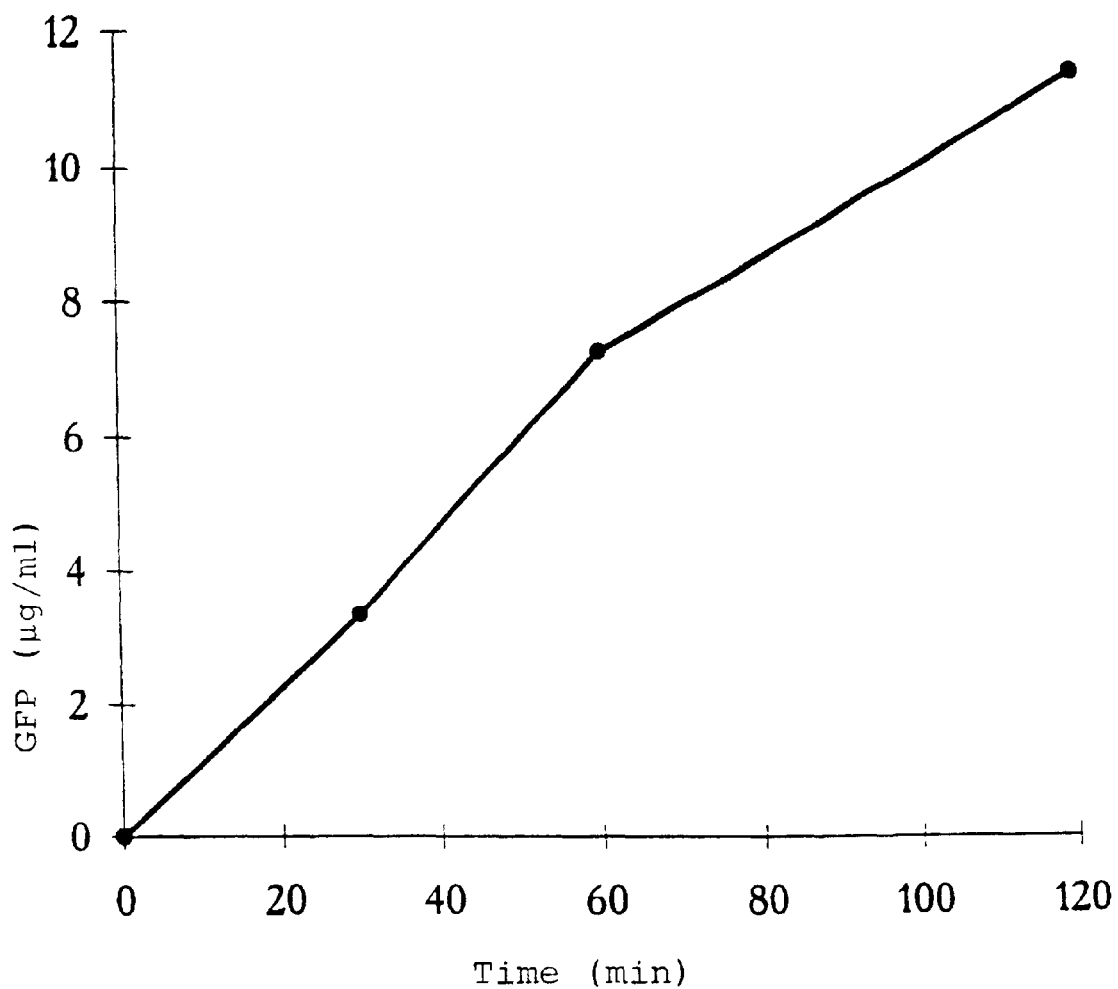
FIG. 8 shows the dependence of the change in the concentration of synthesized GFP on the duration of synthesis in a control aliquot according to the data of Example 1.
Figure 9:
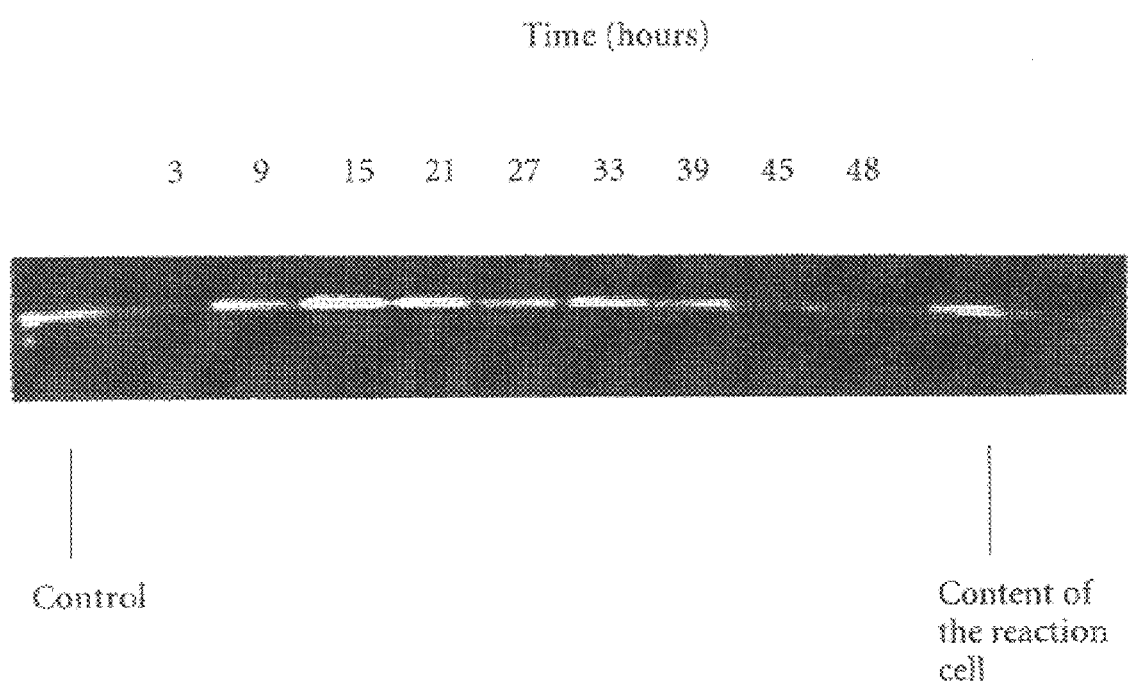
FIG. 9 is a photo of SDS electrophoresis according to the data of Example 1.

The synthesis is carried out at 26° C. in the reaction cell. The feed solution is supplied to the reaction cell at a rate equal to its 1.5–2 internal volumes per 1 hour. The product is extracted at a rate equal to 1/20–1/8 of the internal volume of the cell per 1 hour. During the entire synthesis the specific fluorescence of the product removed through a membrane with the cutoff of 50 kD is recorded. The efficiency of the system is estimated by fluorescence of all assembled volumes. FIG. 7 represents a histogram showing the amount of GTP in fractions collected during synthesis. The amount of GFP in the fractions is estimated by the calibration curve plotted using the data of specific fluorescence measurements of the purified GFP preparation versus its concentration. FIG. 8 shows a diagram of dependence of a change in the concentration of synthesized GFP on the time of synthesis in a control aliquot incubated in a constant volume. The concentration is determined by incorporation of radioactive amino acid in the polypeptide. In addition the newly synthesized product is controlled by registration of fluorescence after electrophoresis of all assembled volumes in polyacrylamide gel. FIG. 9 shows a photo of gel electrophoresis with aliquots selected from fractions collected during synthesis. A purified GFP preparation is used as control. The amount of layered protein is 0.3 mg.

A portion of 150–200 $\mu$g of a functionally active product is obtained during 48 h per 1 ml of the coupled transcription/translation system.

EXAMPLE 2

The coupled transcription/translation of green fluorescent protein (GFP) of coelenterate bacterium *Aequoria victoria* from a DNA template containing a GFP gene in a continuous cell-free system from *E. coli* with one flow.

The DNA is obtained and the coupled transcription/translation system is prepared as described in Example 1. The synthesis is carried out using a device whose block diagram is given in FIG. 3. Hollow fibers of 1 mm in diameter and the cutoff size of 100 kD were used as the first porous barrier in the reactor module. An ultrafiltration membrane with the cutoff size of 10 kD and the area of 4 cm$^2$ were used as the second porous barrier. The reactor volume was 400 μl.

The feed solution flow is supplied to the reaction cell at a rate equal to its 1.5–2 internal volumes per 1 hour. The product is not removed.

Figure 10:
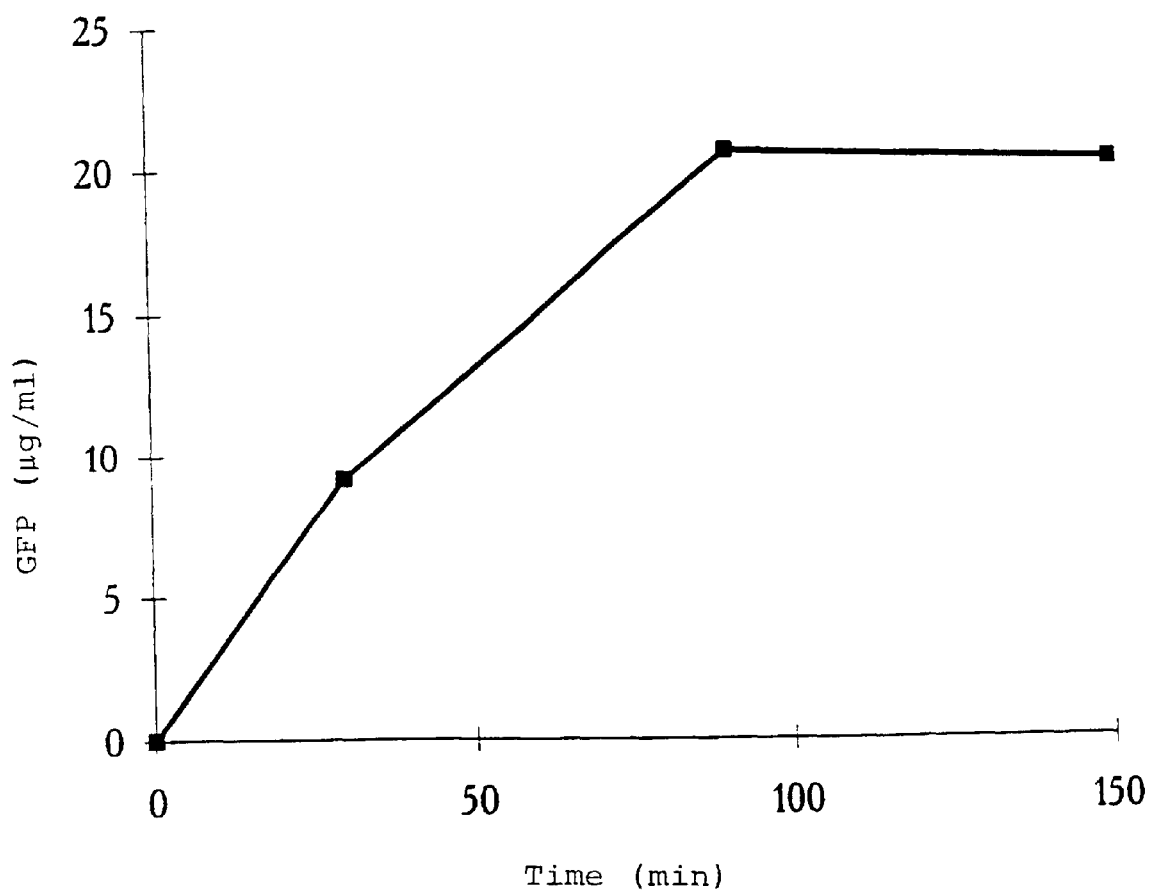
FIG. 10 shows a diagram of dependence of the change in the concentration of synthesized GFP on the duration of synthesis in a control aliquot according to the data of Example 2.
Figure 11:
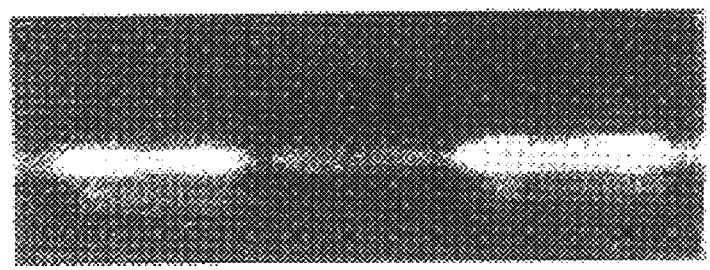
FIG. 11 is a photo of SDS electrophoresis according to the data of Example 2.

The efficiency of the system is estimated from the fluorescence of the solution removed upon termination of synthesis from the reaction cell with a subsequent determination of the amount of the polypeptides synthesized. Then it is compared to the efficiency of control synthesis in a fixed volume. FIG. 10 shows a diagram of dependence of a change in the concentration of synthesized GFP on the duration of synthesis in the control aliquot incubated in a constant volume. The concentration is determined by incorporation of radioactive amino acids in the polypeptide. In addition the newly synthesized product is controlled by recording fluorescence after electrophoresis of all collected volumes in polyacrylamide gel. FIG. 11 represents a photo of gel electrophoresis with aliquots selected from the coupled transcription/translation system in fixed volume and from the reaction cell after termination of synthesis. A purified preparation of GFP is used as control. The amount of layered protein is 0.3 mg.

During synthesis 60 μg of a functionally active product are obtained for 24 h per 1 ml of the coupled transcription/translation system.

REFERENCES

Spirin A. S. et al., A Continuous Cell-Free Translation System Capable of Producing Polypetides in High Yield. Science 242, 1162–1164 (1988)

Spirin A. S. Cell-Free Protein Synthesis Bioreactor. From Frontiers in Bioprocessing II, 31–43, Editors: Todd P. et al. Amer. Chem. Soc. (1992)

Takanori K. et al. A Continuous Cell-Free Protein Synthesis System for Coupled Transcription-Translation. J. Biochem. 110, 166–168 (1991)

Erdmann V. A. et al. The Protein-Bioreactor: Its Potentials for the Synthesis of Proteins in Biotechnology. Medicine and Molecular Biology, First German-Russian Summerschool on In vitro Systems, 64–70, Berlin (1994)

Kim D. et al. A highly efficient cell-free protein synthesis from *Escherichia coli*. Eur. J. Biochem. 239, 881–886 (1996)

Flux Recovery-Cleaning, Sanitization, Storage, Depyrogenation, from UF/MF Operating Guide, A/G Technology Corporation, 16–20 (1997)

Alberts B. et al. Molecular Biology of a Cell. p. 133, New York, London (1983)

Simonenko P. et al., Controlled System for Cell-free Protein Expression: Protein Biosynthesis Reactor, ??? (1998)

Baranov V. I. et al. Gene Expression in a Cell-free System on Preparative Scale. Gene 84: 463–466 (1989)

Kolb V. A. et al., Synthesis and Maturation of Green Fluorescent Protein in a Cell-free Translation System, Biotech. Lett. 18: 1447–1452 (1996)

Zubay G. In vitro Synthesis of Protein in Microbial Systems, Annu. Rev. Genet. 7: 267 (1973)

Crameria A. et al., Improved Green Protein by Molecular Evolution Using DNA Shuffling, Nature Biotech. 14: 315–319 (1996)

PATENTS

Alakhov Yu. B. et al, Method of preparing polypeptides in a cell-free translation system. U.S. Pat. No. 5,478,730, Dec. 26, 1995, U.S. Cl.—435/68.1.

Choi C. et al. Method producing protein in a cell-free system. U.S. Pat. No. 5,593,856, Jan. 14, 1997, U.S. Cl.—435/68.1

Mozayeni B. R. Apparatus and process for continuous in vitro synthesis of proteins U.S. Pat. No. 5,434,079, Jul. 18, 1995, U.S. Cl.—435/311

Fischer K. H. et al. Verfahren zur Beschleunigung des Stoffaustauschs eines kontinuierlichen Bioreaktors and Vorrichtung zur Durchfuhrung dieses Verfahrens. DE Pat. No. 39-4956 A1, Nov. 22, 1990, Int. Cl.—C12 M 1 1/12

Alakhov Y. B. et al. A method of preparing polypeptides in cell-free translation system. SU—1618761 A1, 07.01.91, N1 1991, Int. Cl.—C 12 P 21/02

Baranov V. I. et al. A method of preparing polypeptides in cell-free translation system. EP Patent 0593757, 15.01.1997, Int. Cl. C12P 21/00

Matson S. L. et al. Method and apparatus for conducting catalytic reactions with simultaneous product separation and recovery. U.S. Pat. No. 4,786,597, Nov. 22, 1988, U.S. Cl. 435/041

Wrasidio W. J. et al. Thin film membrane enzyme reactor and method of using same. U.S. Pat. No. 4,956,289, Sep. 11, 1990, U.S. Cl. 435/180

Dziewulski D. et al. Three compartment bioreactor and method of use. U.S. Pat. No. 5,135,853, Aug. 4, 1992, US Cl. 435-04

Hu W. et al. Bioreactor device with application as a bioartificial liver. U.S. Pat. No. 5,605,835, Feb. 25, 1997, U.S. Cl. 435-297,2

Puchinger H. et al. Process for the in -vitro biosynthesis of hormones, especially insulin. U.S. Pat. No. 4,225,671, Sep. 30, 1980, US Cl. 435/71

Pedersen S. K. et al. Cartridge of hybrid unitary wafers of hollow fiber membranes and module containing a stack of post-potted cartridges. U.S. Pat. No. 5,366,625, Nov. 22, 1994, U.S. Cl. 210-321.78

Hargitay B. Ultrafiltration and reverse osmosis device comprising plural carbon tubes bonded together. U.S. Pat. No. 4,341,631, Jul. 27, 1982, U.S. Cl. 210–323.2

Yagihashi T. et al. Separation module and bundle unit of hollow thread-type porous membrane elements and methods of producing same. U.S. Pat. No. 5,584,997, Dec 17, 1997, U.S. Cl. 210–321.79

Hanai T. Bundle of permselective hollow fibers and a fluid separator containing the same. U.S. Pat. No. 5,198,110, Mar. 30, 1993, U.S. Cl. 210–321.79

Gerbhard T. et al. Multi-bioreactor hollow fiber cell propagation system and method, U.S. Pat. No. 5,656,421, Aug. 12, 1997, U.S. Cl. 435/003

Ovodov S. J. et al. Method for obtaining polypeptides in a cell-free translation system. EP Pat. EP 0 485 608 B1, 22. 11.95, Bulletin 95/47, Int. Cl. C12P 21/00.

What is claimed is:

1. A device for synthesis of polypeptides in a cell-free translation system containing at least one reactor module including a reactor volume having an inlet and an outlet for linking liquid circuits and including at least two porous barriers, a system for supply of different fractions of the feed solution and expendable high molecular weight components, consisting of at least one pump, liquid circuits, compartments for accumulation and storage of products or feed solution, wherein the reactor comprises at least one reactor volume, whose external surface contacts the external surface of the first and second porous barriers, the internal surface of the second porous barrier is connected to the zone of the inlet or outlet of low molecular weight flows, the internal side of the first porous barrier is connected to the zone of the inlet and outlet of low molecular weight flows and flows containing high molecular weight components with the target polypeptide.

2. The device according to claim 1 wherein each reactor module has a reactor volume from 50 $\mu$l to 10 ml and the thickness of the reactor layer from 30 $\mu$m to 5 mm.

3. The device according to claim 1 wherein each reactor volume has the shape of either (i) a rectangular sheet, or a square sheet, or a round sheet, or (ii) a sheet folded either in a helix or cylinder.

4. The device according to claim 1 wherein the ratio of the area of the surface of the second porous barrier to the area of the surface of the first porous barrier is from 1 to 100.

5. The device according to claim 1 wherein each reactor volume contains either (i) the reaction mixture, (ii) the reaction mixture with a magnetic stirrer, or (iii) the reaction mixture with a porous extender, or (iv) the reaction mixture with porous granules.

6. The device according to claim 3 wherein each extender is made of porous materials with pore sizes from 200 $\mu$m to 10 nm, these materials are selected from (i) fibrous structures in the form of bundles or sheets, (ii) a composition of fibrous structures with a coating of porous particles, (iii) affinity sorbents in the form of granules or composition of fibrous structures with a coating of affinity sorbents, and (iv) granules with immobilized components of the cell-free system.

7. The device according to claim 1 wherein the above first and second porous barriers are made either from flat membranes or from hollow fibres, or one barrier is made from a membrane and the other barrier is made from hollow fibres.

* * * * *